(12) United States Patent
Koehler et al.

(10) Patent No.: US 12,148,544 B2
(45) Date of Patent: Nov. 19, 2024

(54) STABLE TOP-BRIDGE MANUFACTURING FOR DAX GRATINGS

(71) Applicant: KONINKLIJKE PHILIPS N.V., Eindhoven (NL)

(72) Inventors: Thomas Koehler, Norderstedt (DE); Andriy Yaroshenko, Garching (DE); Gereon Vogtmeier, Aachen (DE); Bernd Rudi David, Grunberg (DE); Juergen Mohr, Aachen (DE); Paulus René Maria Van Beers, Eindhoven (NL); Pascal Meyer, Karlsruhe (DE); Michael Richter, Karlsruhe (DE); Joachim Schulz, Karlsruhe (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 321 days.

(21) Appl. No.: 17/637,988

(22) PCT Filed: Aug. 18, 2020

(86) PCT No.: PCT/EP2020/073041
§ 371 (c)(1),
(2) Date: Feb. 24, 2022

(87) PCT Pub. No.: WO2021/037601
PCT Pub. Date: Mar. 4, 2021

(65) Prior Publication Data
US 2022/0319731 A1    Oct. 6, 2022

(30) Foreign Application Priority Data
Aug. 30, 2019    (EP) .................................. 19194586

(51) Int. Cl.
G21K 1/02      (2006.01)
A61B 6/00      (2006.01)
A61B 6/42      (2024.01)

(52) U.S. Cl.
CPC ............ G21K 1/025 (2013.01); A61B 6/4291 (2013.01); A61B 6/484 (2013.01); *G21K 2201/067* (2013.01)

(58) Field of Classification Search
CPC .................. A61B 6/4291; A61B 6/484; G21K 2207/067; G21K 2201/064; G21K 1/10;
(Continued)

(56) References Cited

U.S. PATENT DOCUMENTS 7,573,976 B2    8/2009   Lacey
8,861,685 B2    10/2014  Pohan
(Continued)

FOREIGN PATENT DOCUMENTS

DE    102015201741 A1    8/2016
EP        3745420 A1 *   12/2020    ............ G21K 1/025
WO      WO2012055495 A1  5/2012

OTHER PUBLICATIONS

PCT International Search Report, International application No. PCT/EP2020/073041, Dec. 1, 2020.
(Continued)

*Primary Examiner* — Don K Wong
(74) *Attorney, Agent, or Firm* — Larry Liberchuk (57) ABSTRACT

In order to improve the mechanical stability of an X-ray grating with top bridges for X-ray dark field imaging and/or X-ray phase contrast imaging, it is proposed to reduce or prevent the undesired high stress on the top bridges by a change in the manufacturing process. Specifically, it is proposed to electroplate the top bridges after the bending. In
(Continued)

other words, the electroplating of the top bridges is performed on the bent geometry.

14 Claims, 6 Drawing Sheets

(58) Field of Classification Search
CPC ........ G21K 1/067; G01N 23/041; C25D 5/02; C25D 5/16; C25D 5/10; C25D 7/00; C25D 11/00
See application file for complete search history.

(56) References Cited

U.S. PATENT DOCUMENTS

| | | |
|---|---|---|
| 8,989,353 B2 | 3/2015 | Kaneko |
| 9,506,878 B2 | 11/2016 | Teshima |
| 2010/0246769 A1 | 9/2010 | David |
| 2011/0194673 A1 | 8/2011 | Teshima |
| 2015/0316494 A1 | 11/2015 | Teshima |
| 2016/0027546 A1 | 1/2016 | Teshima |
| 2016/0349197 A1 | 12/2016 | Litamura |

OTHER PUBLICATIONS

Pfeiffer F. et al., "Phase Retrieval and Differential Phase-Contrast Imaging with Low-Brilliance X-Ray Sources." Nature Physics, vol. 2, No. 4, pp. 258-261, Apr. 2006.

* cited by examiner

STABLE TOP-BRIDGE MANUFACTURING FOR DAX GRATINGS

FIELD OF THE INVENTION

The present invention relates to a method for producing an X-ray grating for an imaging apparatus for X-ray dark field imaging and/or X-ray phase contrast imaging. The invention further relates to a microstructure produced by the method, an imaging apparatus, a method of performing X-ray phase contrast and/or dark field imaging.

BACKGROUND OF THE INVENTION

Grating-based phase-contrast and dark-field X-ray (DAX) imaging is a promising technology to enhance the diagnostic quality of X-ray equipment, e.g., in the areas of mammography, chest radiography, and computer tomography (CT). One of the most challenging problems to build a clinical system based on this technology is the manufacturing of the gratings. In particular, the source grating G0 and the absorption grating G2 may require grating structures with pitches in the order of a few µm to a few 10 µm at heights in gold of more than 200 µm in order to achieve sufficient attenuation across the entire spectrum of the X-ray tube, especially if the tube provides photons in the energy range above 30 to 40 keV.

Polymer structures (resist structures) fabricated by lithography may be used for grating manufacturing by filling the polymer template with a strong X-ray absorbing material (e.g. gold). If the grating is used as source grating G0, it was observed that the resist cannot withstand the thermal and radiation load, and the entire grating becomes unstable. Therefore, it is planned to strip off the resist after electroplating. To ensure mechanical stability of the grating lamellae, they need to be connected by electroplating additional bridges on top of the gratings. In order to access the full field of view, the source grating G0 needs to be bent. However, the bent top bridges may be subject to high mechanical stress.

SUMMARY OF THE INVENTION

There may be a need to improve the mechanical stability of an X-ray grating with top bridges for X-ray dark field imaging and/or X-ray phase contrast imaging.

The object of the present invention is solved by the subject-matter of the independent claims, wherein further embodiments are incorporated in the dependent claims. It should be noted that the following described aspects of the invention apply also for the method for producing an X-ray grating, the microstructure, the imaging apparatus, the method of performing X-ray phase contrast and/or dark field imaging.

A first aspect of the present invention provides a method for producing an X-ray grating for an imaging apparatus for X-ray dark field imaging and/or for X-ray phase contrast imaging. The method comprises the steps of:
 a) producing a resist negative grating that has a plurality of periodically arranged grating webs and grating openings on a flat sample;
 b) filling the grating openings on the flat sample by electroplating, by continuing the electroplating up to the height of the grating webs for forming grating lamellae;
 c) processing on top of the resist negative grating a form which enables introducing top bridges substantially perpendicular to the grating webs;
 d) bending the resist negative grating to a desired radius; and
 e) filling the form by electroplating to form the top bridges after bending the resist negative grating.

In other words, it is proposed to reduce or prevent the undesired high stress on the top bridges by a change in the manufacturing process. Specifically, it is proposed to electroplate the top bridges after the bending. In other words, the electroplating of the top bridges is performed on the bent geometry. The detailed manufacturing process will be explained hereafter and particularly with respect to the exemplary embodiments in FIG. 1 and FIGS. 2A to 2G.

It will be appreciated that the above operation may be performed in any suitable order, e.g., consecutively, simultaneously, or a combination thereof, subject to, where applicable, a particular order being necessitated, e.g., bending before the top bridges being electroplated.

For example, it is possible to exchange steps b) and c). The process will be as follows:
 a1) producing a resist negative grating that has a plurality of periodically arranged grating webs and grating openings on a flat sample, i.e. step a);
 b1) processing on the top of the resist negative grating a form, which enables introducing top bridges substantially perpendicular to the grating webs, i.e. step c);
 c1) filling the grating openings on the flat sample by electroplating, by continuing the electroplating up to the height of the grating webs for forming grating lamellae, i.e. step b);
 d1) bending the resist negative grating to a desired radius, i.e. step d); and
 e1) filling the form by electroplating to form the top bridges after bending the resist negative grating, i.e. step e).

It is also noted that some steps may be performed simultaneously. For example, it is possible to fabricate the form for the top bridges directly after manufacturing the resist negative grating and electroplating both the grating openings and the form of the top bridges in one step. The process will be as follows:
 a2) producing a resist negative grating that has a plurality of periodically arranged grating webs and grating openings on a flat sample, i.e. step a);
 b2) processing on top of the resist negative grating a form, which enables introducing top bridges substantially perpendicular to the grating webs, i.e. step c);
 c2) bending the resist negative grating to a desired radius, i.e. step d);
 d2) filling the grating openings on the flat sample by electroplating for forming grating lamellae, and filling the form by continuing the electroplating to form the top bridges, i.e. steps b) and e) in one step.

According to an embodiment of the present invention, the method further comprises the step of removing the resist negative grating between the grating lamellae after performing the electroplating.

According to an embodiment of the present invention, in step d), a frame is provided that allows precise bending the resist negative grating to the desired radius.

As the electroplating of the top bridges has to be done in the bent geometry, it may be beneficial to have a frame, e.g., for the G0 structure, that allows for precise bending to the final radius, and that is compatible to the mounting position in the imaging apparatus close to the X-ray tube.

According to an embodiment of the present invention, the bending radius of the frame is compatible to a mounting position in the imaging apparatus close to an X-ray tube.

According to an embodiment of the present invention, the frame is of a non-conductive material, or the frame is fully covered by a non-conductive material.

As the electroplating after bending has to be limited to the areas of the top bridges and not on other surfaces of the frame, special material, such as non-conductive material, or a non-conductive coated frame, may be used and some protection of areas where no electroplating should apply have to be made. Examples of the non-conductive material may include plastic, glass, ceramics, etc.

According to an embodiment of the present invention, step e) further comprises selecting a temperature for the electroplating. The selected temperature is chosen such that geometry changes and/or mechanical stress of the X-ray grating are at or near a minimum in an operating condition of the X-ray grating in the imaging apparatus.

The X-ray grating, such as G0, is typically used in a holder close to the X-ray tube (at the X-ray window). The X-ray tube will be operated under different conditions and will heat up e.g. from room temperature to about 70° C. On the other side, there are transport conditions with a broader temperature range. The temperature changes (transport-static, operation-slow dynamic) should have minimum effect on the deformation of the grating and the stabilizing bridges, such that the expansion of the bridge should not bend the lamellae in the ideal situation. For example, it may be preferable to use the nominal "0" deformation then at a temperature condition of 40° C. to have only limited bending with +/−20° changes, such that the impact on bending and with that on the X-ray beam formation would be minimized.

Similar for the vibration of the X-ray tube during operation, it may be desirable to avoid resonance frequencies in bridges and gratings that would be in the range of the anode rotation frequency during operation.

For the electroplating, a temperature has to be selected to allow good plating conditions. However, the temperature that allows good plating conditions may not be suitable for achieving a desirable mechanical property of the top bridges, since the properties of the electroplated top bridges are also dependent on the temperature for electroplating. Accordingly, an overall tradeoff may be selected between allowing good plating conditions and solving expected stress situations.

The effect of the plating process conditions on e.g. thermal and mechanical properties of electroplated top bridges, such as residual stress, the modulus of elasticity, thermal expansion and the like, may be simulated and investigated by e.g. a finite-element analysis. The effect of the plating process conditions on the thermal and mechanical properties of electroplated top bridges may also be investigated based on experimental results. Based on the properties of the electroplated top bridges and their relationship with process conditions, it is possible to select a temperature for electroplating to achieve desired properties (e.g. thermal and mechanical properties) of electroplated top bridges for solving expected stress situations. In other words, for the overall mechanical design of the bent structure, it may be required to optimize the complete design of the X-ray grating such that geometry changes and mechanical stress due to temperature changes and/or mechanical vibration are at or near a minimum in an operating condition of the X-ray grating in the imaging apparatus.

In an example, the temperature for electroplating may be selected to fabricate an X-ray grating that has only limited bending with +/−5°, +/−10°, +/−20°, or other changes at a temperature condition of 40° C.

In an example, the temperature for electroplating may be defined such that for the fabricated X-ray grating, the resonance frequencies in bridges and gratings are not in the range of the anode rotation frequency during operation.

In an example, the temperature for electroplating may be selected to fabricate an X-ray grating that has only limited bending with +/−5°, +/−10°, +/−20°, or other changes at a temperature condition of 40° C. and the resonance frequencies in bridges and gratings are not in the range of the anode rotation frequency during operation.

According to an embodiment of the present invention, the top bridges are shaped such that mechanical stress due to the top bridges is at or near a minimum in an operating condition of the X-ray grating in the imaging apparatus.

In other words, the selection of the shape of the top bridges may have an effect on the stresses generated. Therefore, for the overall mechanical design of the bent structure, it may be required to optimize the shape design of the top structures to have minimal impact on geometry changes and mechanical stress due to temperature changes and mechanical vibration during operation of the imaging system.

The shape of the top bridges may be modified with thickness variation and bridge profile optimization to allow temperature expansion but less lamellae deformation depending on the stiffness of the bridge design. Slightly bended bridge like a spring could minimize the stress at the interface to the lamella compared to zero-tolerance distances. The shape may be adapted according to e.g. temperature ranges of the tube, vibration of the system, g-forces during tube positioning, etc., for reducing the mechanical stress in an operating condition of the X-ray grating in the imaging apparatus.

According to an embodiment of the present invention, the top bridges and the grating lamellae are fabricated out of a same material.

For materials compatibility, it may make sense to fabricate also the bridges in the same material. Thus, a strong X-ray absorbing material (e.g. gold) may be used for both the top bridges and the grating lamellae.

According to an embodiment of the present invention, the grating lamellae are electroplated in a high X-ray absorbing material. The top bridges are electroformed in a low X-ray absorbing material.

In other words, the selection of the material of the top bridges may also have an effect on the stress generated. Thus, the selection of the material and the geometry of the top bridges is a tradeoff between the imaging properties and the mechanical properties for the stabilizing effect of the bridge in the bent geometry. Examples of the imaging properties include low absorption in the trench and the top bridges, no bending of the absorbing walls, and no vibration of walls and lifetime stability in same position. Examples of the mechanical properties include compensating the influence of temperature, vibration, static and dynamic stress, thermal expansion, etc. Therefore, for the overall mechanical design of the bent structure, it may be required to optimize the selection of the material of the top structures to have minimal impact on geometry changes and mechanical stress due to temperature changes and mechanical vibration during operation of the imaging system.

According to an embodiment of the present invention, the resist negative grating comprises a plurality of stabilizing structures for stabilizing the webs.

The top bridges may be applied to any type of resist negative gratings, including resist negative gratings with e.g. bridges or sunrays stabilizing structures.

According to an embodiment of the present invention, the stabilizing structures comprise a bridge structure and/or a sunray structure.

According to an embodiment of the present invention, the bending in step d) is positive bending or negative bending.

A further aspect of the present invention provides a microstructure produced by the method as described above and below.

With the proposed manufacturing process, the top bridges of the microstructure are less subject to high mechanical stress. This can reduce the risk for the homogeneity of the microstructure, as there is less chance that the top bridges will enter the ductile regime at different bending radius. In other words, the microstructure has improved mechanical stability.

A further aspect of the present invention provides an imaging apparatus for capturing an image of a subject, comprising:
  an X-ray source;
  a source grating;
  a diffraction grating for diffracting X-rays emitted from the X-ray source;
  an absorption grating for absorbing a part of the X-rays diffracted by the diffraction grating; and
  a detector for detecting the X-rays, which have passed through the absorption grating;
  wherein at least one of the source grating, the diffraction grating, and the absorption grating comprises a microstructure according to any one of the above and below described exemplary embodiments and examples.

The imaging apparatus may be provided for medical or non-medical applications (e.g. non-destructive testing). The imaging apparatus may be in a stationary geometry like planar X-ray and/or rotating CT like system. As the microstructure has improved mechanical stability, the phase information detected by the imaging system is less subject to temperature changes and mechanical vibration during operation of the imaging apparatus.

A further aspect of the present invention provides a method of performing X-ray phase contrast and/or dark field imaging, comprising:
  positioning a subject between the source grating and the diffraction grating or between the diffraction grating and the absorption grating of an imaging apparatus according to any one of the above described exemplary embodiments and examples;
  emitting an X-ray beam onto the subject; and
  detecting the X-ray beam having passed through the subject, the source grating, the diffraction grating, and the absorption grating of the imaging apparatus for acquiring image data.

As used herein, the term "substantially" refers to the complete or nearly complete extent or degree of a state as indicated. For example, a reference that top bridges are substantially perpendicular to the grating webs would mean that the top bridges are substantially perpendicular to carry out a particular function, i.e. to provide additional mechanical stability. The exact allowable degree of deviation from absolute completeness may depend on the desired mechanical stability and manufacturing tolerance. For example, a deviation of ±5° from absolute completeness may be considered to be substantially perpendicular. In some cases, for example, when high mechanical stability is desired, a deviation of ±0.1° from absolute completeness may be considered to be substantially perpendicular.

Furthermore, herein the term "near" a minimum refers to preferably 10% from the minimum, more preferably 5%, even more preferably 1%, and most preferably 0% from the minimum.

These and other aspects of the present invention will become apparent from and be elucidated with reference to the embodiments described hereinafter.

BRIEF DESCRIPTION OF THE DRAWINGS

These and other aspects of the invention will be apparent from and elucidated further with reference to the embodiments described by way of examples in the following description and with reference to the accompanying drawings, in which.

It should be noted that the figures are purely diagrammatic and not drawn to scale. In the figures, elements which correspond to elements already described may have the same reference numerals. Examples, embodiments or optional features, whether indicated as non-limiting or not, are not to be understood as limiting the invention as claimed.

DETAILED DESCRIPTION OF EMBODIMENTS

As mentioned above, if the grating is used as source grating G0, it was observed that the resist cannot withstand the thermal and radiation load, and the entire grating becomes unstable. Therefore, it is planned to strip off the resist after electroplating to ensure mechanical stability of the grating lamellae by electroplating additional bridges on top of the gratings. Actually, the simulation using the finite element method (FEM) shows that for a small bending radius, there is even the risk that the material in the top bridges leaves the elastic regime and enters the ductile regime. This is a particular risk for the homogeneity of the grating since there will be always variations in the thickness of the bridges, which implies that the bridges will enter the ductile regime at different bending radius. In addition, there are stresses due to the top bridges, which lead to inacceptable inclination of the grating lamella.

Figure 1:
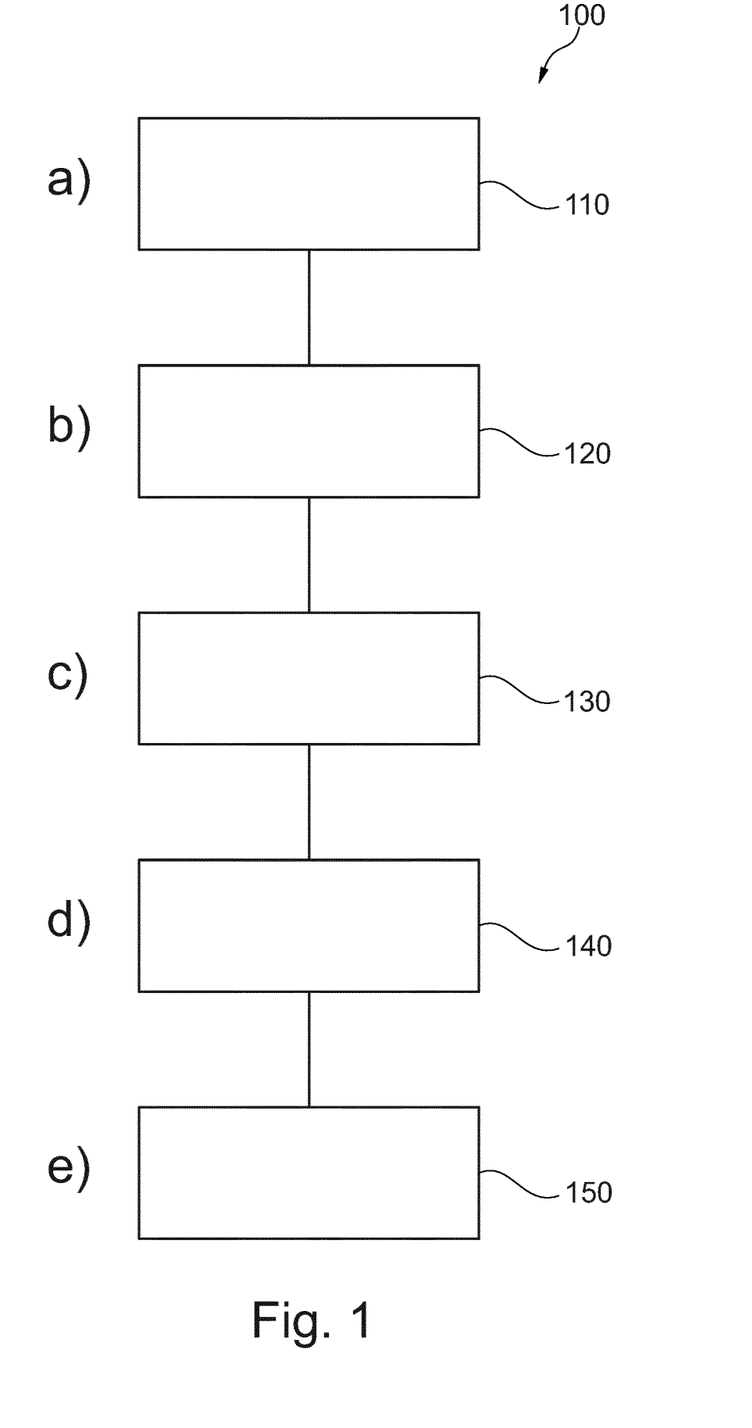
FIG. 1 shows a flow chart of a method for producing an X-ray grating for an imaging apparatus for X-ray dark field imaging and/or for X-ray phase contrast imaging.

To enhance the mechanical stability of the fabricated X-ray gratings, FIG. 1 shows a flow chart of a method 100 for producing an X-ray grating for an imaging apparatus for X-ray dark field imaging and/or for X-ray phase contrast imaging. The following steps have also been described with reference to the exemplary embodiments in FIG. 2A-2G.

Figure 2A:
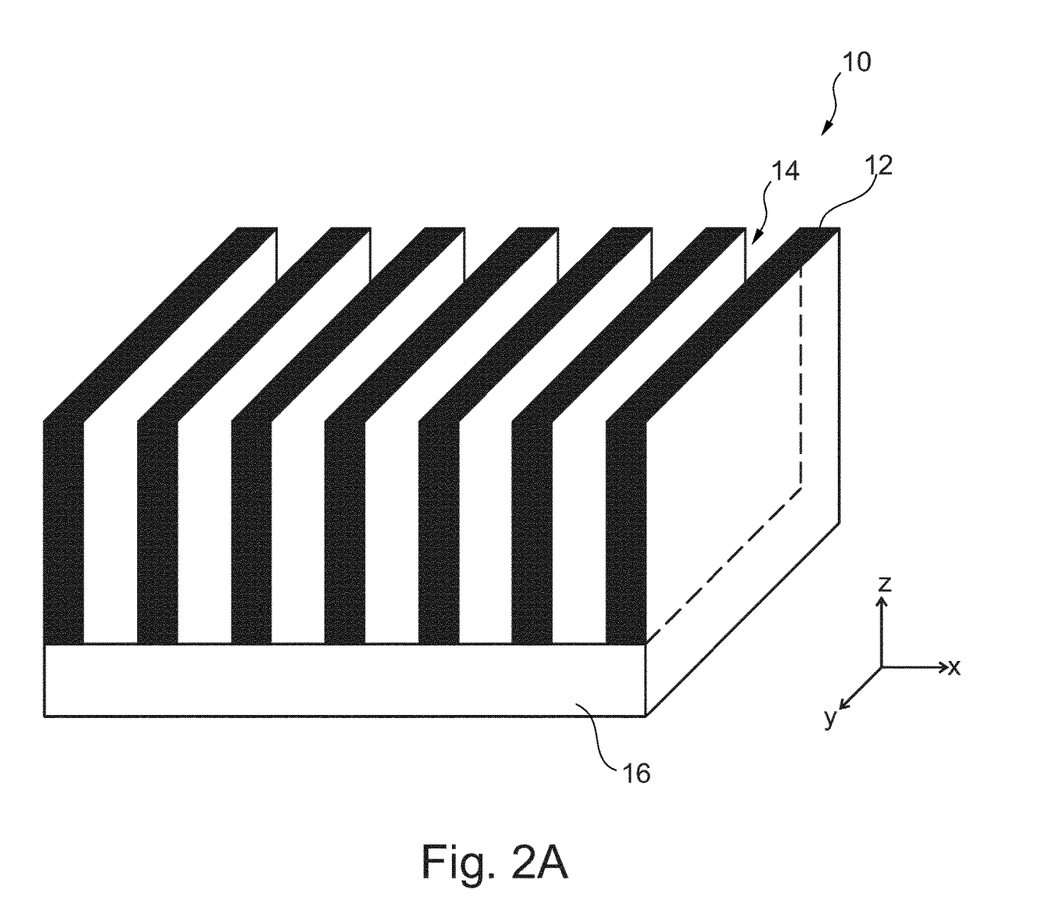
FIG. 2A-2G show a method for producing an X-ray grating according to an exemplary embodiment of the present disclosure.
Figure 2B:
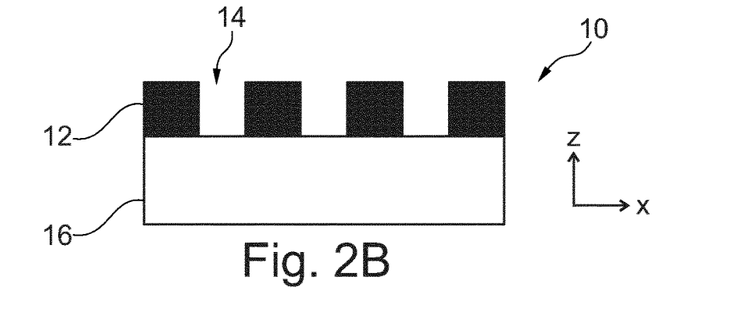

In step 110, i.e. step a), a resist negative grating is produced that has a plurality of periodically arranged grating webs and grating openings on a flat sample. FIG. 2A illustrates a perspective view of an example of a resist negative grating 10, and FIG. 2B illustrates a front view of the resist negative grating 10 in the XZ plane. The resist negative grating 10 has a plurality of periodically arranged grating webs 12 and grating openings 14 on a flat sample 16, such as a silicon substrate. The grating webs 12 may also be referred to as resist lamellae. The grating webs 12 form a resist structure, which may be a polymer structure. The shape, size, and/or pattern of the periodically arranged grating webs 12 are determined based on the structure of a desired X-ray grating. In the example of FIG. 2A, the resist negative grating 10 has a resist structure for manufacturing a one-dimensional grating. In another example (not shown), the pattern may be constituted by a periodic structure of a square pattern, the period of which may be approximately 1 µm to 10 µm and the height of which may be approximately more than 200 µm. The resist negative grating 10 may also have stabilizing structures for stabilizing the resist (not shown). One example of the stabilizing structure is a bridge structure. Another example of the stabilizing structure is a sunray structure.

Figure 2C:
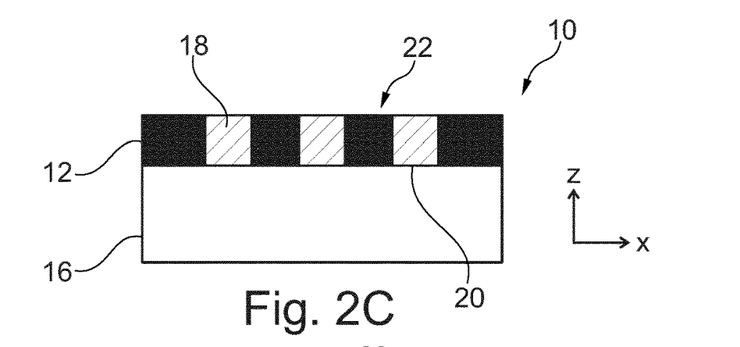

In step 120, i.e. step b), the grating openings on the flat sample are filled by electroplating, by continuing the electroplating up to the height of the grating webs for forming grating lamellae. As illustrated in FIG. 2C, grating lamellae 18, i.e. metal microstructure, are formed by electrolytic plating the grating openings 14 of the resist negative grating 10 with a metal from the surface 20 of the flat sample 16, while using the resist negative grating 10 as a mold. As a result, a fine metal microstructure can be manufactured within the grating openings 14, i.e. the recessed portion, of the resist negative grating 10. The metal may be embodied by X-ray absorbing metals, such as Ag or Mo, preferably with a high absorption coefficient, such as Pb, Bi, or W. It is preferred that the X-ray absorbing metals also enable a formation of a microstructure by electrolytic plating. However, electroplating capabilities of the different materials are quite different. Hence, the metal selection may be a tradeoff between X-ray absorbing capabilities and electroplating capabilities.

Figure 2D:
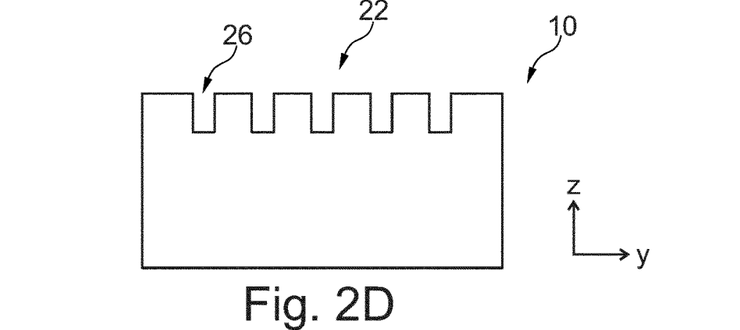

In step 130, i.e. step c), a form is processed on top of the resist negative grating. The form enables introducing top bridges substantially perpendicular to the grating webs. For example, FIG. 2D illustrates a side view of the resist negative grating 10 in the YZ plane. A form 26 is process on top 22 of the resist negative grating 10. The form 26 may have one or more small trenches or openings in a rectangular shape or any other suitable shape with the width of the top bridges. This may be processed with a laser. Another option may be the combination of mask and specific etching. The form may be further processed to achieve optimized functionality for mechanical stabilization and cleaned interface to allow electroplating interface of the existing grating webs 12 to the top bridges. Once the form 26 is created, the grating lamellae 18 are connected by trenches or openings, which can be filled to form top bridges.

Figure 2E:
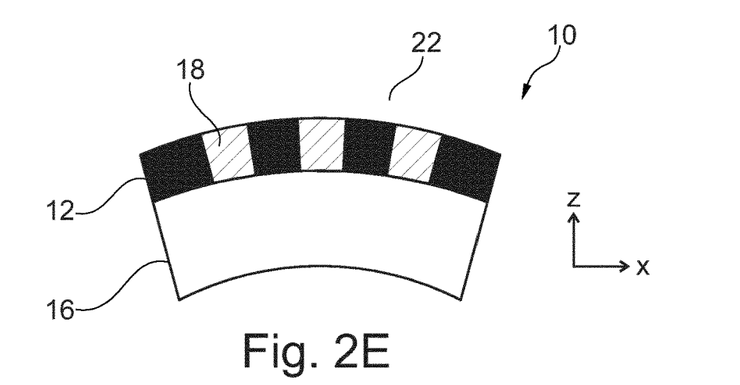

In step 140, i.e. step d), the resist negative grating is bent to a desired radius. An example of the bent resist negative grating 10 is illustrated in FIG. 2E, which again illustrates a front view of the resist negative grating 10 in the XZ plane. It is also noted that the bending may be positive bending (not shown), i.e. the upper side of the resist negative grating is compressed and the lower one stretches, or negative bending, i.e. the upper side of the resist negative grating stretches and the lower one compresses as illustrated in FIG. 2E.

Figure 2F:
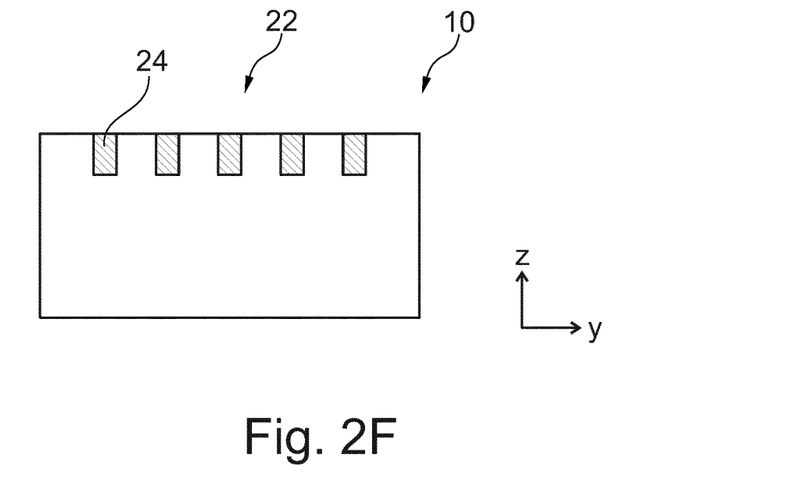

In step 150, i.e. step e), after bending the resist negative grating, the form is filled by electroplating to form the top bridges after bending the resist negative grating. FIG. 2F now illustrates the side view of the resist negative grating in the YZ plane. Top bridges 24 are formed on the top 22 of the resist negative gratings 10. As the electroplating of the top bridges 24 has to be done in the bent geometry, a frame (not shown) may be required for the G0 structure that on the one hand allows for precise bending to the final radius, and that is compatible to the mounting position in the imaging apparatus close to the X-ray tube. On the other hand, the electroplating after the bending has to be limited to the areas of the top bridges and not on other surfaces of the frame. Special materials, such as non-conductive material like plastics, glass, or ceramics, may be used for protecting areas where no electroplating should be applied. Alternatively, a non-conductive coated frame may be used for protecting areas where no electroplating should be applied. In other words, an exposed surface is limited to the areas of top bridges on the top 22 of the resist negative grating 10, and the other portions including the back surface of the resist negative gratings may be all covered with the non-conductive material, or with the non-conductive coated frame. Therefore, in the electrolytic plating, the metal can be deposited only from the exposed surface, i.e. the areas of top bridges.

As an option, the resist negative grating 10 between the grating lamellae 18 may be removed after performing the electroplating, i.e., after step 150.

Figure 2G:
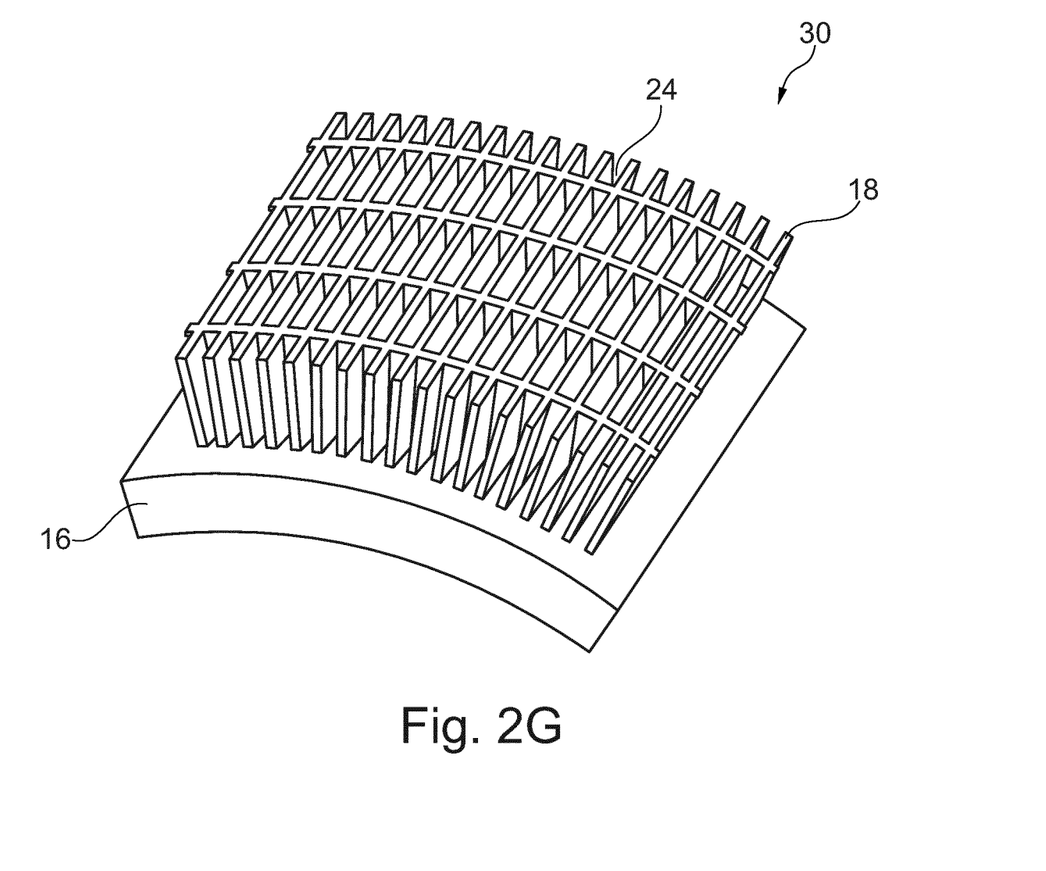

FIG. 2G shows an example of an X-ray grating 30 produced by the method described above and below after stripping the resist. For illustration purpose, the bending is shown in FIG. 2G outwards whereas the desired bending direction will be inwards. A plurality of top bridges 24 is introduced on the top of the grating lamellae 18. The top bridges 24 are substantially perpendicular to grating lamellae 18 to ensure the mechanical stability. The shape, size, and pattern of the top bridges 24 are determined based on a desired mechanical stability to be achieved in an operating condition of the X-ray grating in the imaging apparatus. As previously mentioned, the top bridges may have a shape adapted for reducing the mechanical stress in an operating condition of the X-ray grating in the imaging apparatus. The material of the top bridges may also be selected to have an effect on the stresses generated. FEM simulations may be helpful to find the desired shape and/or material of the top bridges.

In this way, the undesired high stress on the top bridges can be prevented by a change in the manufacturing process, particularly by electroplating the top bridges after bending. A microstructure produced by the above method has less stress on the top bridges. Thus, for a large bending radius, there is less risk that the material in the top bridges leaves the elastic regime and enters the ductile regime. This may be particularly beneficial for the homogeneity of the grating, since there will be always variations in the thickness of the top bridges. In other words, the homogeneity of the microstructure is less subject to the temperature changes and mechanical vibration during operation of the imaging system. Thus, the mechanical stability of the microstructure is improved.

It will be appreciated that the above operation may be performed in any suitable order, e.g., consecutively, simultaneously, or a combination thereof, subject to, where applicable, a particular order being necessitated, e.g., bending before the top bridges being electroplated.

Thus, it is possible to interchange some of the processing steps. For example, it is also possible to exchange steps b) and c). The process will be as follows: a)→c)→b)→d)→e). In another example, it is also possible bend the resist negative grating earlier, i.e., to do also the electroplating of the grating lamellae after bending. The process will be as follows: a)→c)→d)→a combination of b) and e). That is to say, the basic idea remains to bend the resist negative grating before the top bridges being electroplated.

Further approaches may be used to optimize the mechanical stability of the top bridges in an operating condition of the X-ray grating.

As an example, in general, for the electroplating, a temperature has to be selected to allow good plating conditions. However, the temperature for the electroplating in step 150 may be selected such that geometry changes and/or mechanical stress of the X-ray grating are at or near a minimum in an operating condition of the X-ray grating in the imaging apparatus. For example, it may be considered to optimize a complete design of the X-ray grating to have less impact on geometry changes and mechanical stress due to temperature changes and/or mechanical vibration in an operating condition of the X-ray grating in the imaging apparatus. The optimization may be carried out based on the properties of the electroplated top bridges and their relationship with process conditions. For example, the temperature for electroplating may be selected to achieve desired mechanical properties of electroplated top bridges for solving expected stress situations.

However, the optimal electroplating temperature for allowing good plating conditions and the optimal electroplating temperature for achieving desired mechanical properties of electroplated top bridges may be different. Therefore, an overall tradeoff may be selected between allowing good plating conditions and solving expected stress situations.

As another example, a special shape of the top bridges may minimize the stress in the operating condition and may be prepared either pre-processing the top-wall interface areas and/or with post-process, such as temporal change of the electroplating conditions. The shape (or geometry) of the top bridges may be optimized with thickness variation and bridge profile optimization to allow temperature expansion but less lamellae deformation depending on the stiffness of the bridge design. Slightly bended bridge like a spring could minimize the stress at the interface to the lamella compared to zero-tolerance distances. The shape may be adapted according to e.g. temperature ranges of the tube, vibration of the system, g-forces during tube positioning, etc., for reducing the mechanical stress in an operating condition of the X-ray grating in the imaging apparatus.

As a further example, the grating webs are usually fabricated in high X-ray absorbing material, such as Au. For materials compatibility, it may make sense to fabricate also the bridges in the same material. This may raise the problem that absorption due to the top bridges may have an effect of imaging performance. Therefore, it may be beneficial to electroform the top bridges in less absorbing material like e.g. nickel. The selection of material of the top bridges may also have an effect on the stresses generated. Therefore, the material selection is a tradeoff between the imaging properties and the mechanical properties for the stabilizing effect of the bridge in the bent geometry.

Figure 3:
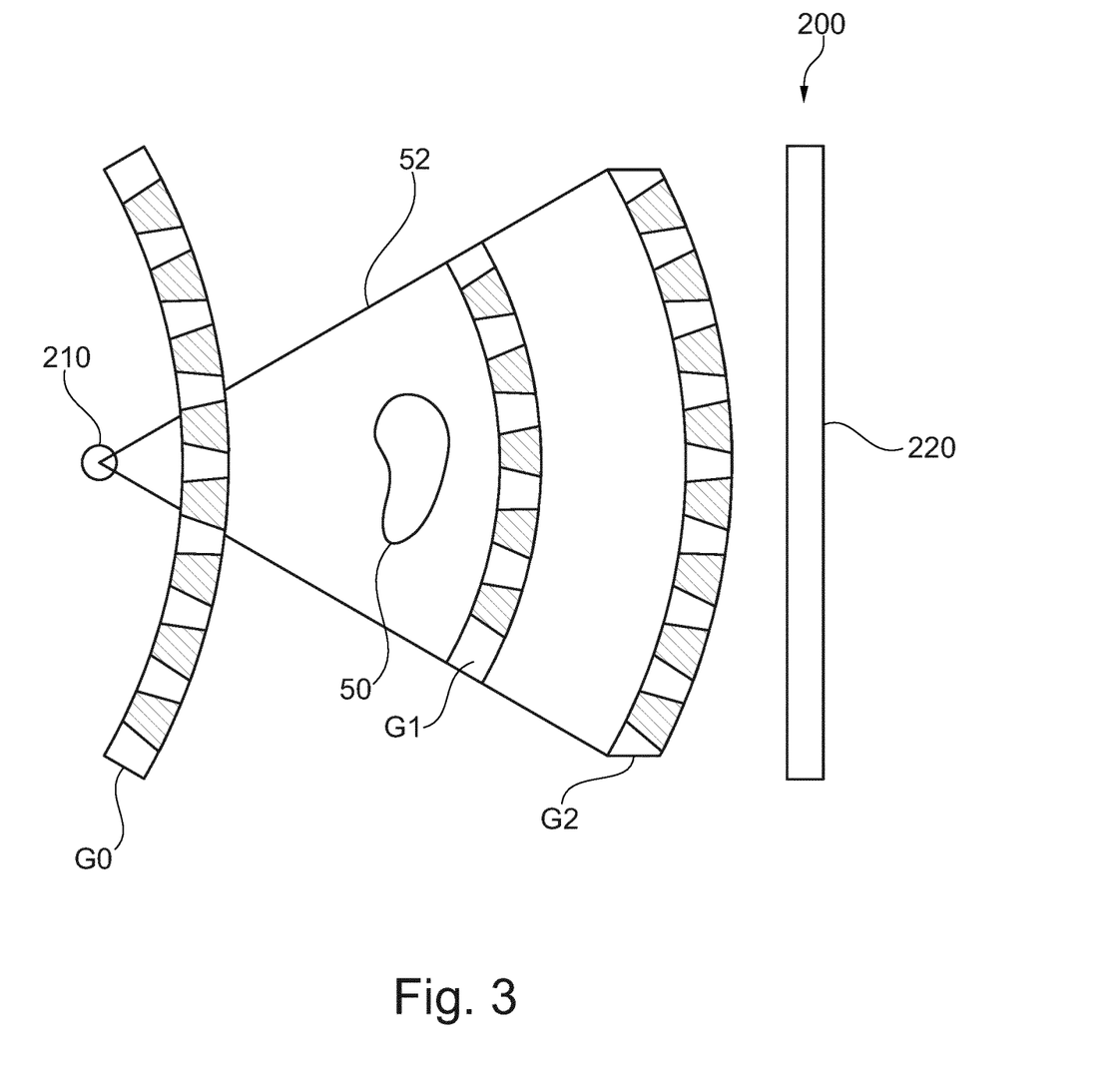
FIG. 3 shows an example of a structure of an imaging apparatus.

In the following, an imaging apparatus utilizing an X-ray Talbot interference method will be described with reference to FIG. 3. FIG. 3 schematically illustrates a configuration of an imaging apparatus 200 using the microstructure manufactured in the above-described exemplary embodiments or examples as at least one of a source grating G0, a diffraction grating G1, and an absorption grating G2.

The imaging apparatus 200 according to the present exemplary embodiments includes an X-ray source 210 for emitting spatially coherent X-rays with the help of the source grating G0, a diffraction grating G1 for periodically modulating the phase of the X-rays, an absorption grating G2 in which an X-ray absorption portion (shield portion) and a transmission portion are arranged, and a detector 220 for detecting the X-rays. Any one of the source grating G0, the diffraction grating G1, and the absorption grating G2 may comprise the microstructure manufactured by the above described exemplary embodiments or examples. Preferably, at least the source grating G0 comprises the microstructure, which can improve the mechanical stability of the source grating G0 and thus the image quality.

The imaging apparatus may be a medical or non-medical imaging apparatus. The imaging apparatus may be in a stationary geometry like planar X-ray and/or rotating CT like system.

As previously discussed, the homogeneity of the microstructure is less subject to the temperature changes and mechanical vibration during operation of the imaging apparatus. Thus, the phase information detected by the imaging apparatus is less subject to the temperature changes and mechanical vibration during operation of the imaging apparatus. In other words, the uncertainty in the phase detection during operation of the imaging apparatus may be reduced, and image quality may be improved.

Figure 4:
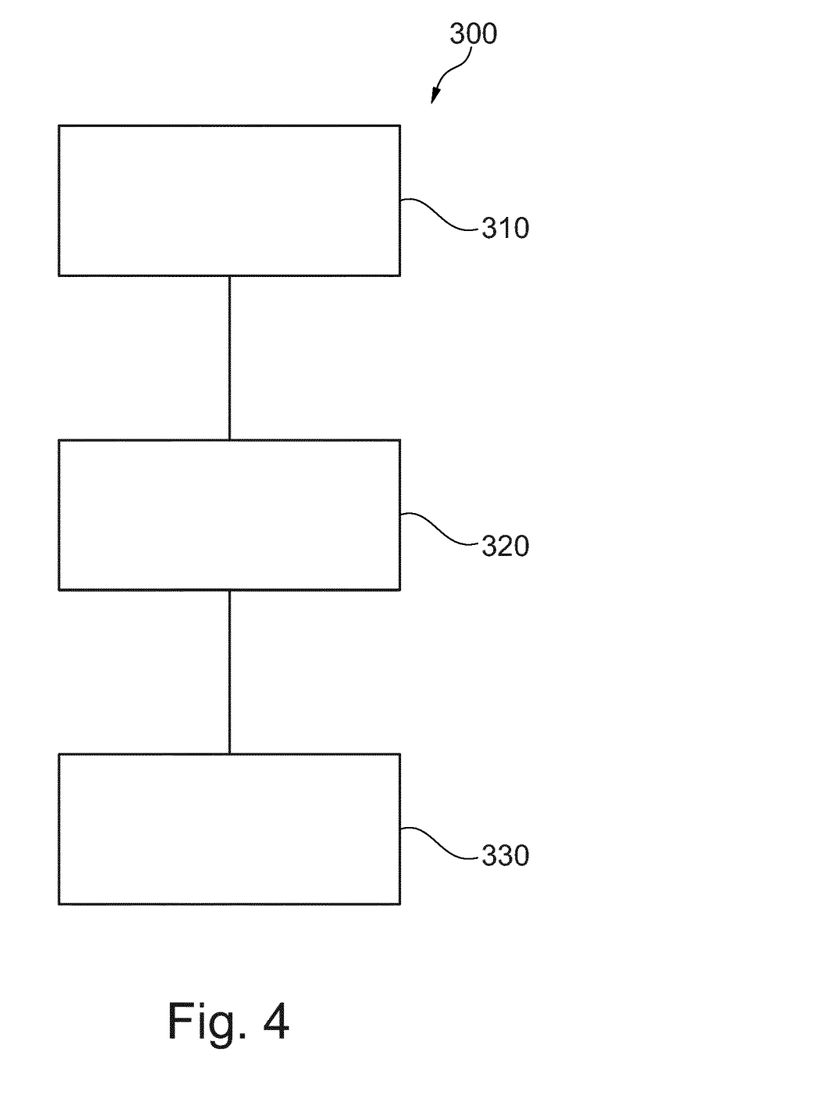
FIG. 4 shows a flow chart of a method for performing X-ray phase contrast and/or dark field imaging.

FIG. 4 illustrates a flow chart of a method 300 for performing X-ray phase contrast and/or dark field imaging. The following steps have also been described with reference to the exemplary imaging apparatus 200 in FIG. 4.

In step 310, a subject 50 is positioned between the source grating G0 and the diffraction grating G1. Alternatively, the subject 50 may be positioned between the diffraction grating G1 and the absorption grating G2.

In step 320, an X-ray beam 52 is emitted onto the subject 50.

In step 330, information about X-ray phase shift due to the subject 50 is detected as Moiré pattern by the detector 220. In other words, this imaging apparatus captures an image of the subject 50 by imaging Moiré pattern, which holds phase information of the subject 50. Execution of phase retrieval processing, such as Fourier transform based on this detection result enables a phase image of the subject to be obtained. Additional processing for phase detection is done according to known phase contrast detection technologies.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for producing an X-ray grating for an imaging apparatus for X-ray dark field imaging and/or for X-ray phase contrast imaging, the method comprising:
   producing a resist negative grating that has a plurality of periodically arranged grating webs and grating openings on a flat sample;
   filling the grating openings on the flat sample by electroplating, by continuing the electroplating up to the height of the grating webs for forming grating lamellae;
   processing on top of the resist negative grating a form, which enables introducing top bridges substantially perpendicular to the grating webs;
   bending the resist negative grating to a desired radius; and
   filling the form by electroplating to form the top bridges after bending the resist negative grating.

2. The method according to claim 1, further comprising: removing the resist negative grating between the grating lamellae after performing the electroplating.

3. The method according to claim 1, wherein a frame is provided that allows precise bending the resist negative grating to the desired radius.

4. The method according to claim 3, wherein the bending radius of the frame is compatible to a mounting position in the imaging apparatus close to an X-ray tube.

5. The method according to claim 3, wherein the frame is of a non-conductive material, or the frame is fully covered by a non-conductive material.

6. The method according to claim 1, further comprising selecting a temperature for the electroplating, wherein the selected temperature is chosen such that geometry changes and/or mechanical stress of the X-ray grating are at or near a minimum in an operating condition of the X-ray grating in the imaging apparatus.

7. The method according to claim 1, wherein the top bridges are shaped such that mechanical stress due to the top bridges is at or near a minimum in an operating condition of the X-ray grating in the imaging apparatus.

8. The method according to claim 1, wherein the top bridges and the grating lamellae are fabricated out of a same material.

9. The method according to claim 1, wherein the grating lamellae are electroplated in a high X-ray absorbing material, and wherein the top bridges are electroformed in a low X-ray absorbing material.

10. The method according to claim 1, wherein the resist negative grating comprises a plurality of stabilizing structures for stabilizing the webs.

11. The method according to claim 10, wherein the stabilizing structures comprise a bridge structure and/or a sunray structure.

12. The method according to claim 1, wherein the bending is positive bending or negative bending.

13. An imaging apparatus for capturing an image of a subject, comprising:
   an X-ray source;
   a source grating;
   a diffraction grating for diffracting X-rays emitted from the X-ray source;
   an absorption grating for absorbing a part of the X-rays diffracted by the diffraction grating; and
   a detector for detecting the X-rays passing through the absorption grating;
   wherein at least one of the source grating, the diffraction grating, and the absorption grating is manufactured by a process comprising:
      producing a resist negative grating that has a plurality of periodically arranged grating webs and grating openings on a flat sample;
      filling the grating openings on the flat sample by electroplating, by continuing the electroplating up to the height of the grating webs for forming grating lamellae;
      processing on top of the resist negative grating a form, which enables introducing top bridges substantially perpendicular to the grating webs;
      bending the resist negative grating to a desired radius; and
      filling the form by electroplating to form the top bridges after bending the resist negative grating.

14. The method according to claim 1, further comprising positioning a subject between the source grating and the diffraction grating or between the diffraction grating and the absorption grating.

* * * * *